US00PP32161P3

(12) United States Plant Patent
Tufaro

(10) Patent No.: US PP32,161 P3
(45) Date of Patent: Sep. 8, 2020

(54) STRAWBERRY PLANT NAMED 'NSG 207'

(50) Latin Name: ***Fragaria* x *ananassa* Duchesne ex Rozier**
Varietal Denomination: NSG 207

(71) Applicant: Nova Siri Genetics S.r.l., Nova Siri (MT) (IT)

(72) Inventor: Nicola Tufaro, Nova Siri (IT)

(73) Assignee: NOVA SIRI GENETICS S.R.L., Nova Siri (MT) (IT)

( * ) Notice: Subject to any disclaimer, the term of this patent is extended or adjusted under 35 U.S.C. 154(b) by 0 days.

(21) Appl. No.: 16/501,378

(22) Filed: Apr. 3, 2019

(65) Prior Publication Data

US 2019/0327868 P1 Oct. 24, 2019

(30) Foreign Application Priority Data

Apr. 23, 2018 (QZ) ..... PBR 2018/1110

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./156, 208
See application file for complete search history.

(56) References Cited

U.S. PATENT DOCUMENTS

PP16,558 P3 5/2006 Lopez

*Primary Examiner* — Susan McCormick Ewoldt
*Assistant Examiner* — Karen M Redden
(74) *Attorney, Agent, or Firm* — Buchanan Ingersoll & Rooney P.C.

(57) ABSTRACT

A new and distinct variety of strawberry plant, referred to by its cultivar name, 'NSG 207', is provided which forms in abundance attractive semi-early-ripening large, medium red primarily conical to slightly rhomboid fruit having firm flesh that is longer than broad in configuration. The growth habit is upright. Medium vigor and medium density is exhibited. White inflorescence is displayed. Commonly a calyx is displayed which is slightly larger than the diameter of the corolla when open. The new variety is particularly well suited for the commercial industry.

14 Drawing Sheets

Figure 1:
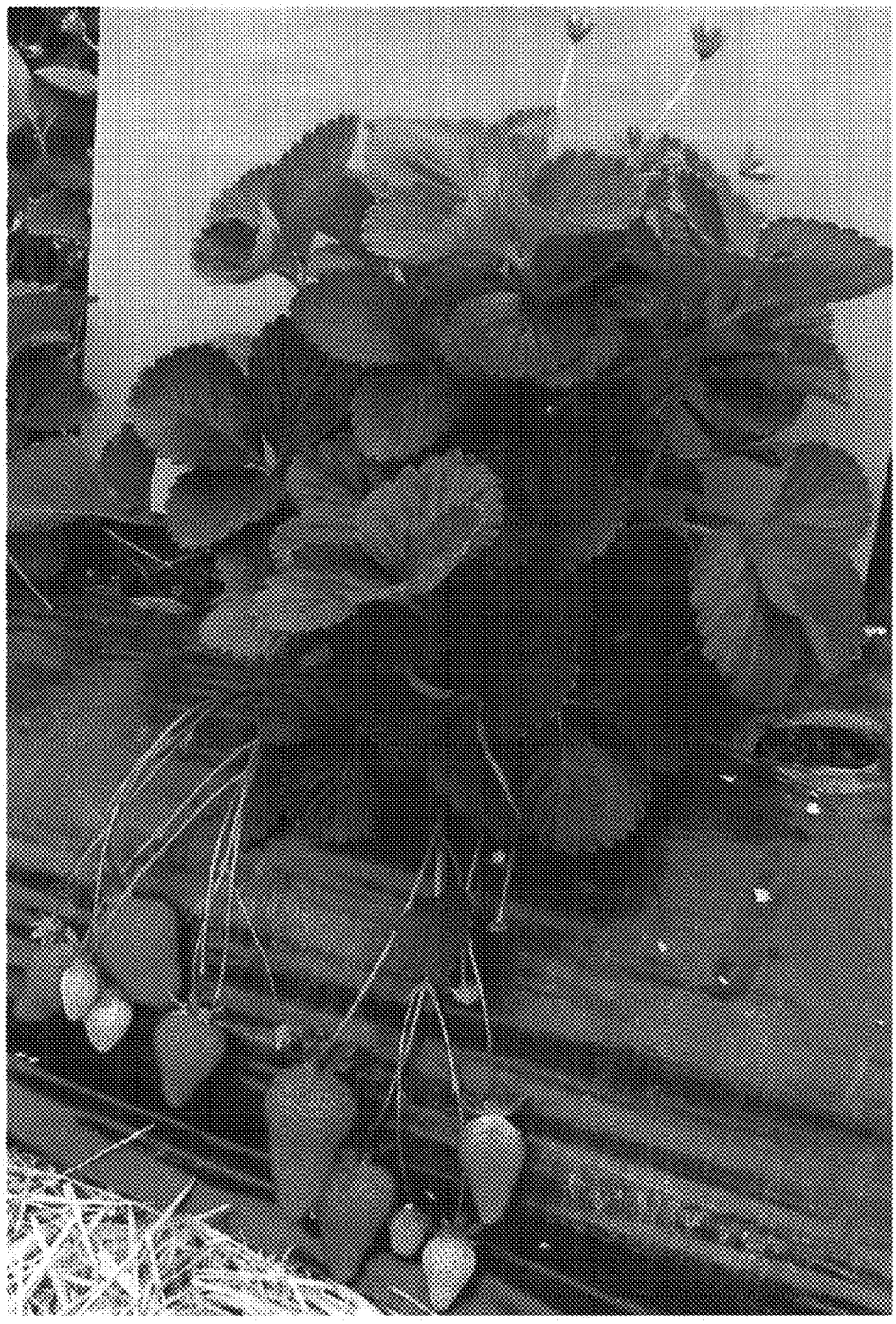

Botanical/commercial classification:
Latin name—*Fragaria* x *ananassa* Duchesne ex Rozier.
Varietal denomination: 'NSG 207'.

CROSS-REFERENCE TO RELATED APPLICATIONS

This application claims priority to Community Plant Variety Rights Application Number 2018/1110 which was filed in European Union through Community Plant Variety Office on Apr. 23, 2018, of which the content of is hereby expressly incorporated by reference in its entirety for all purposes.

SUMMARY OF THE INVENTION

The new and distinct short-day strawberry plant variety of the present invention was the product of a controlled breeding program that was carried out at Nova Siri (MT), Italy located at 40° 08' 40" N-16° 39' 40" E and 10 meters above sea level, wherein two parents were crossed which previously had been studied in the hope that they would contribute the desired characteristics. The female parent (i.e., the seed parent) was the SIRIS variety (non-patented in the United States and European Union Community Plant Variety Rights No. 34843), which is a strawberry variety plant with medium late-season yield and produces fruit with very high contents of sugar and exhibits high tolerance to infection by fungus, such as *Phytophthora cactorum* and *Colletotrichum acutatum*. The male parent (i.e., pollen parent) was the 488P.11.10 variety, which was initially designated as '07-366' (not patented in the United States or Europe and not released), which is a strawberry variety with early to medium season yield, produces very high yield and large primary and secondary fruits.

The parentage can be summarized as follows:

'SIRIS' x '488P.11.10'.

The seeds resulting from the above pollination were sown and small plants were obtained which were physically different from each other. Selective study and testing resulted in the identification of a single short-day strawberry plant of the new variety.

It was found that the new strawberry plant of the present invention possesses the following combination of characteristics:

(a) exhibits a medium vigor, medium density, and an upright growth habit,
(b) displays, on an early basis, white inflorescence at a level generally above the foliage,
(c) commonly displays a calyx that is slightly larger than the diameter of the corolla when open, and
(d) forms in abundance attractive semi-early-ripening large, medium red primarily conical to slightly rhomboid fruit having firm flesh that is longer than broad in configuration.

The new variety well meets the needs of the horticultural industry. The new variety possesses characteristics that commonly are sought by commercial strawberry growers. For example, the new variety provides uniform attractive firm medium red, medium-ripening fruit in good yields, wherein the fruit has good shelf-life. Accordingly, the new variety is to be freshly consumed and considered promising for commercial introduction. The new variety requires an induction period for flowering. This may be achieved by growing in a colder climate away from the equator or at a higher altitude above sea level.

The new variety can be readily distinguished from its ancestors. More specifically, the 'SIRIS' variety (i.e., the seed parent) displays shorter inflorescence than the new variety and exhibits leaflets with crenate margin and the color of the upper surface is commonly near Green Group 141A to Green Group 141B, whereas the new variety displays leaflets with serrate to crenate margin and the color is commonly near Green Group 143A to Green Group 143B. Additionally, the '488P.11.10' variety (i.e., the pollen parent) provides very vigorous vegetation and exhibits a calyx and corolla which are of similar size, whereas the new variety provides medium vigor vegetation and exhibits a calyx which has a larger diameter than the diameter of the corolla. Moreover, the new variety can be readily distinguished from non-parental related similar varieties. For example, the 'Sabrosa' variety (U.S. Plant Pat. No. 16,558) provides fruit with a medium sized inner cavity and exhibits a calyx and corolla which are of similar size, whereas the new variety provides fruit with a small to absent inner cavity and exhibits a calyx which has a larger diameter than the diameter of the corolla.

The new variety has been found to undergo asexual propagation in Poland and Italy by a number of routes, including by use of stolons and in vitro tissue culture. Specifically, the new variety has been asexually reproduced by the use of stolons at Zielona Gora-Ochla, Poland located at 51° 848 N-15° 447 E and at Nova Siri (MT), Italy by in vitro tissue culture. No rooting problems were observed. The combination of characteristics exhibited by the new variety has been found to be stable and reliably transmitted to succeeding generations following such asexual reproduction. Accordingly, the new variety undergoes asexual propagation in a true-to-type manner by such asexual reproduction.

The new variety has been named 'NSG 207'. The new plant variety initially was designated as 488.P.14.207.

BRIEF DESCRIPTION OF THE PHOTOGRAPHS

The accompanying photographs show, as nearly true as it is reasonably possible to make the same in color illustrations of this character, typical specimens of the new variety. The illustrated strawberry plants of the new variety were asexually reproduced from stolons and were planted under the cover of plastic tunnels during mid-October 2017 at Nova Siri (MT), Italy located at 40° 08' 40" N-16° 39' 40" E at 10 meters above sea level.

FIG. 1—illustrates a semi-upright flowering and fruiting plant on Mar. 18, 2018, wherein the newly formed flowers are commonly disposed above the foliage.

Figure 2:
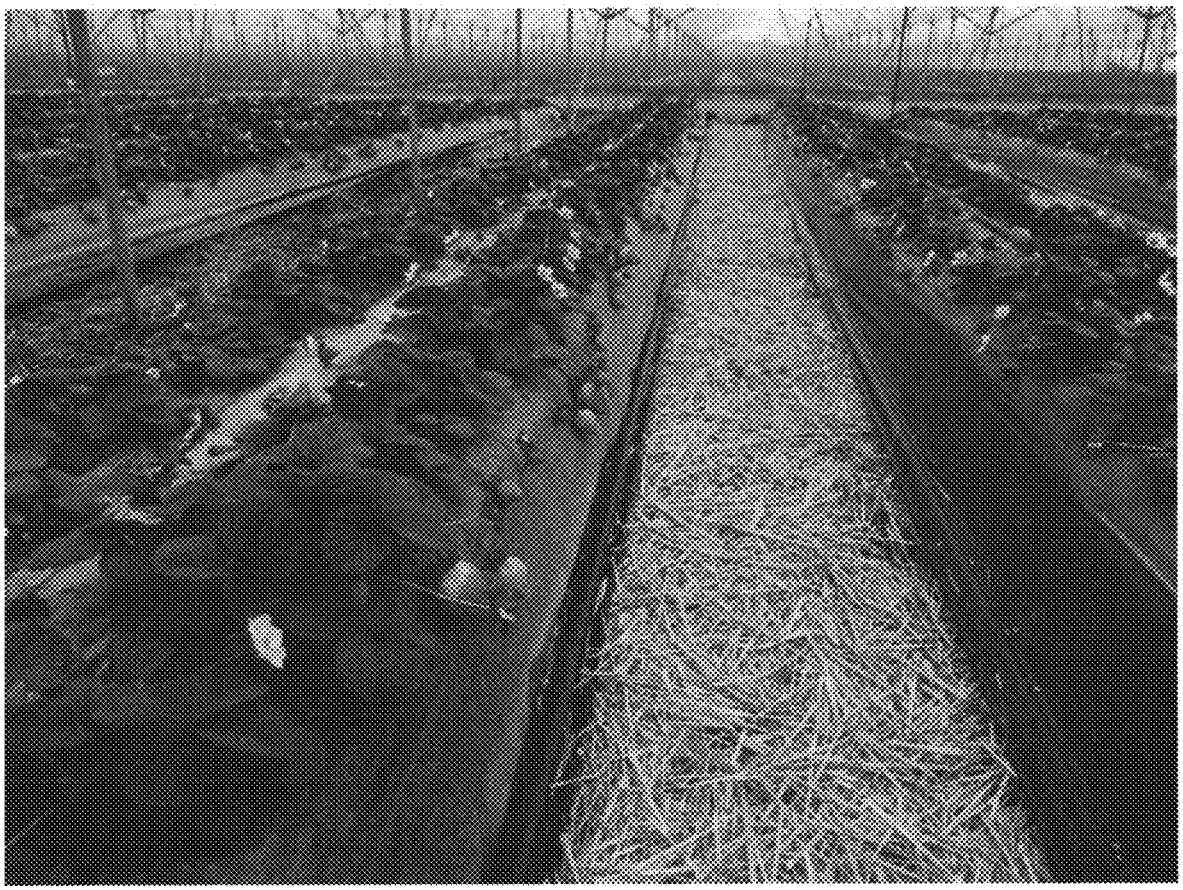

FIG. 2—illustrates rows of early fruiting plants on Jan. 23, 2018, wherein abundant early fruit production is apparent.

Figure 3:
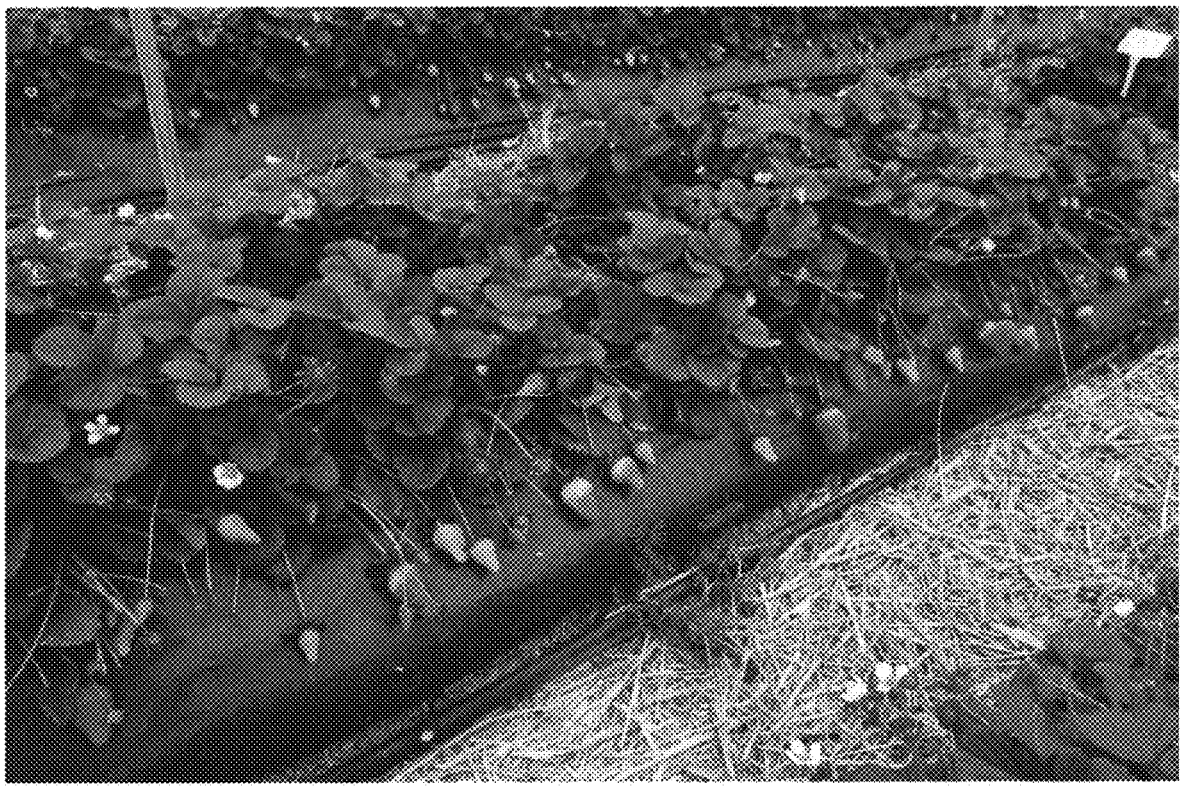

FIG. 3—illustrates a row of fruiting plants on Mar. 8, 2018, wherein uniform vegetation, newly formed flowers, and generally uniform fruit apparent.

Figure 4:
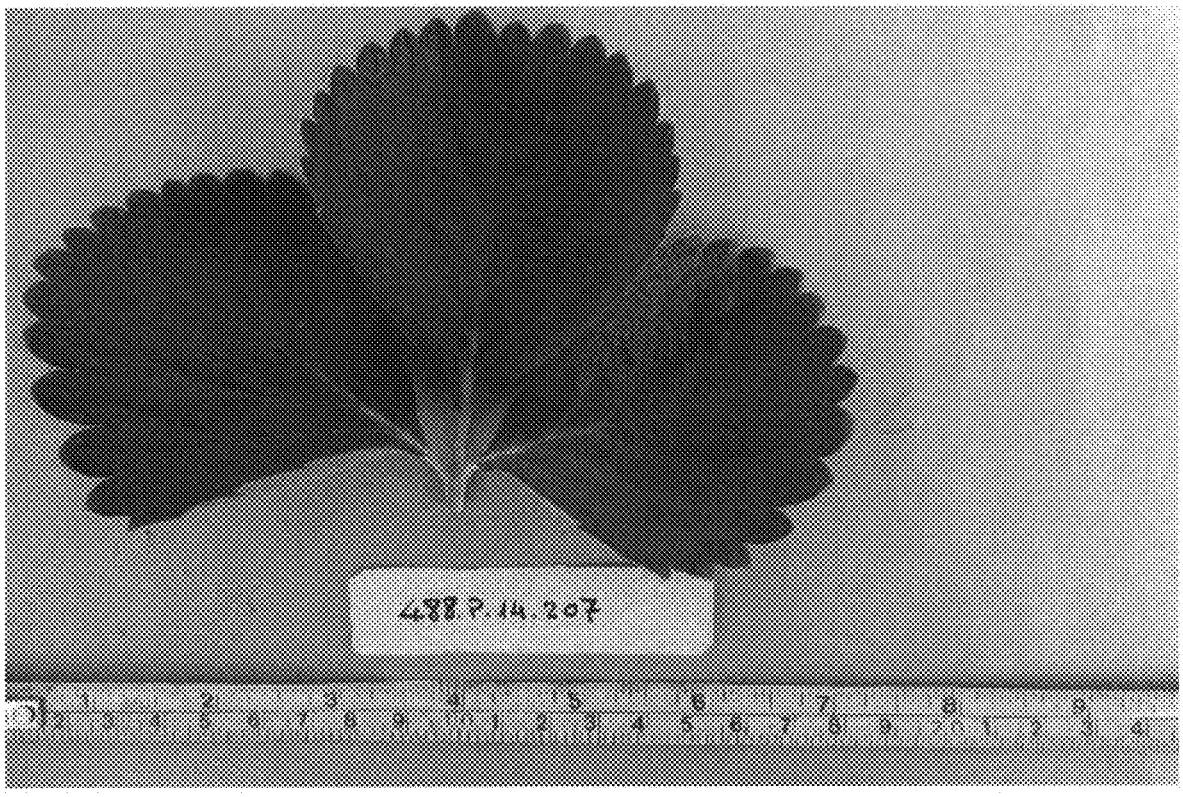

FIG. 4—illustrates a specimen of a three-leaflet leaf—upper surface (designate in image as 488.P.14.207). Dimensions in centimeters and inches are included.

Figure 5:
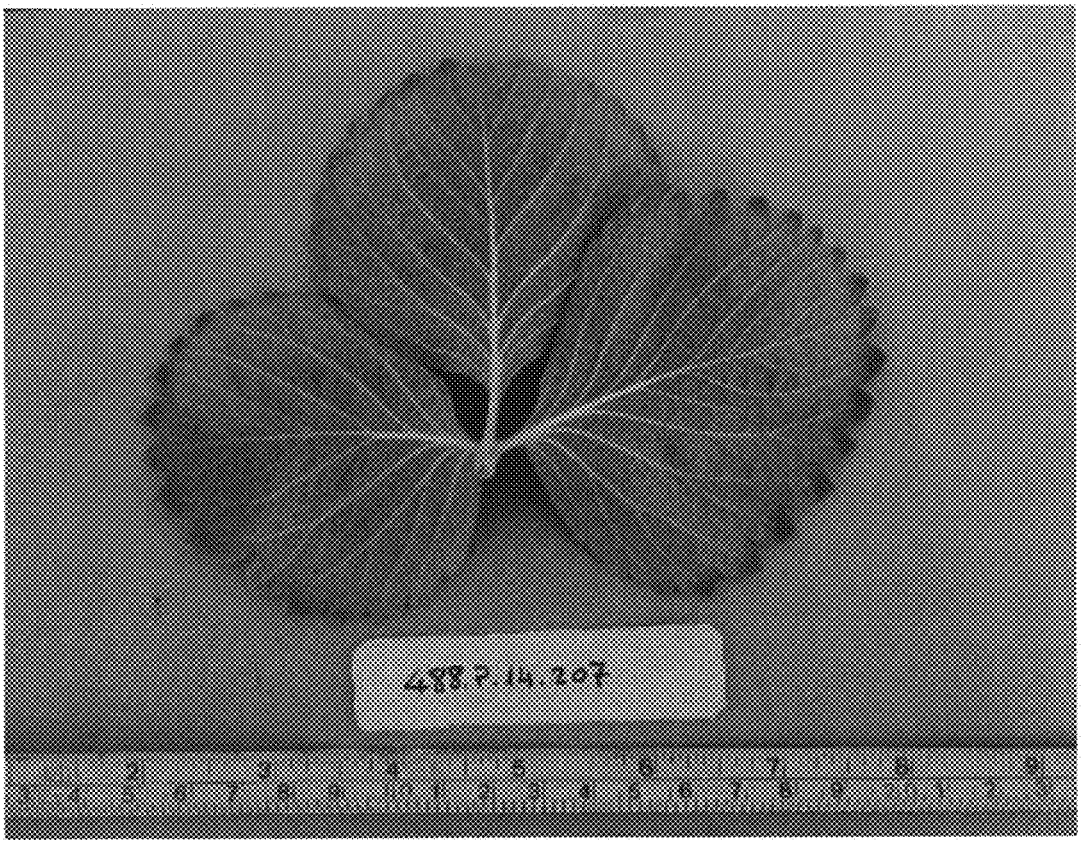

FIG. 5—illustrates a specimen of a typical three-leaflet leaf—under surface (designate in image as 488.P.14.207). Dimensions in centimeters and inches are included.

Figure 6:
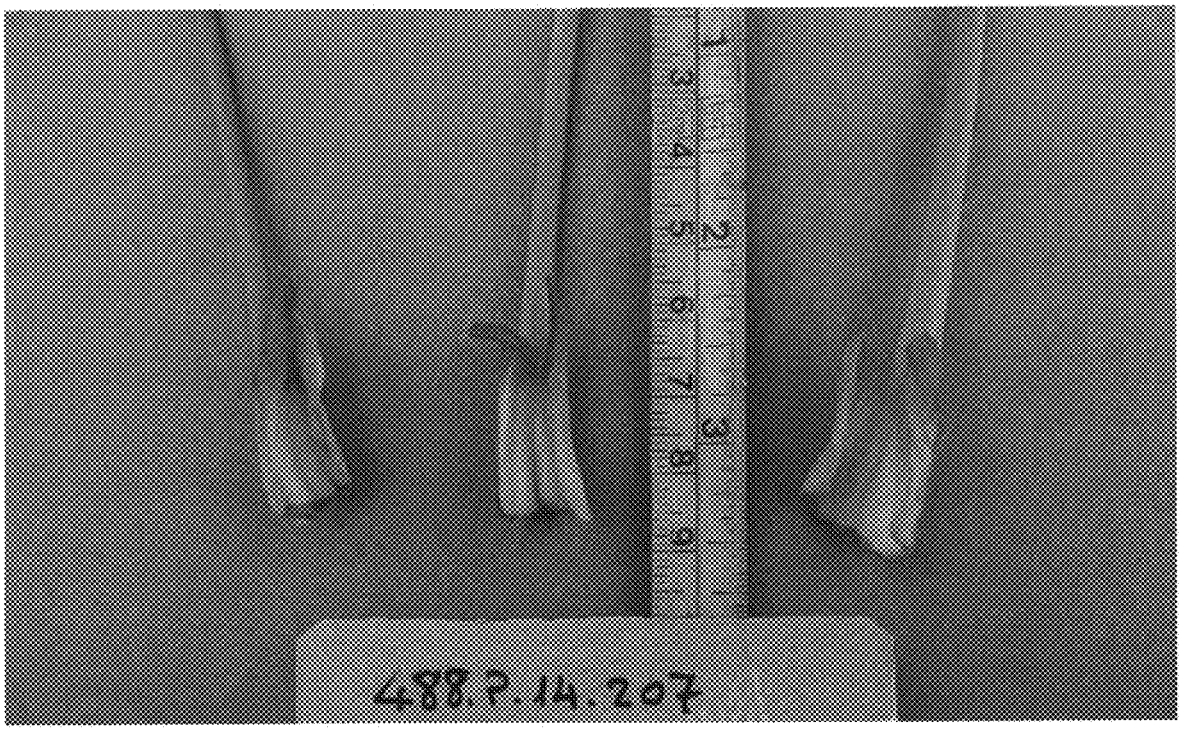

FIG. 6—illustrates specimens of a typical petioles and stipules—close view (designate in image as 488.P.14.207), wherein anthocyanin coloration is apparent. Dimensions in centimeters and inches are included.

Figure 7:
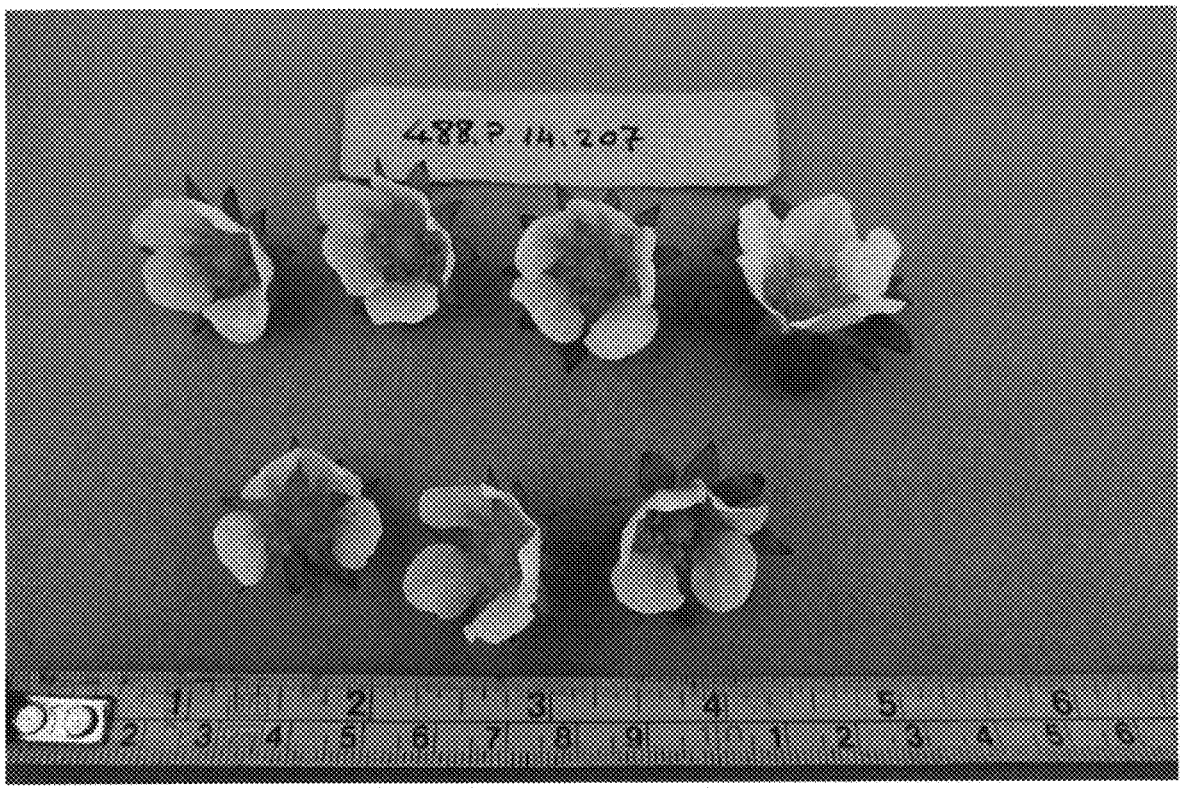

FIG. 7—illustrates specimens of flowers—top, close view (designate in image as 488.P.14.207). Dimensions in centimeters and inches are included.

Figure 8:
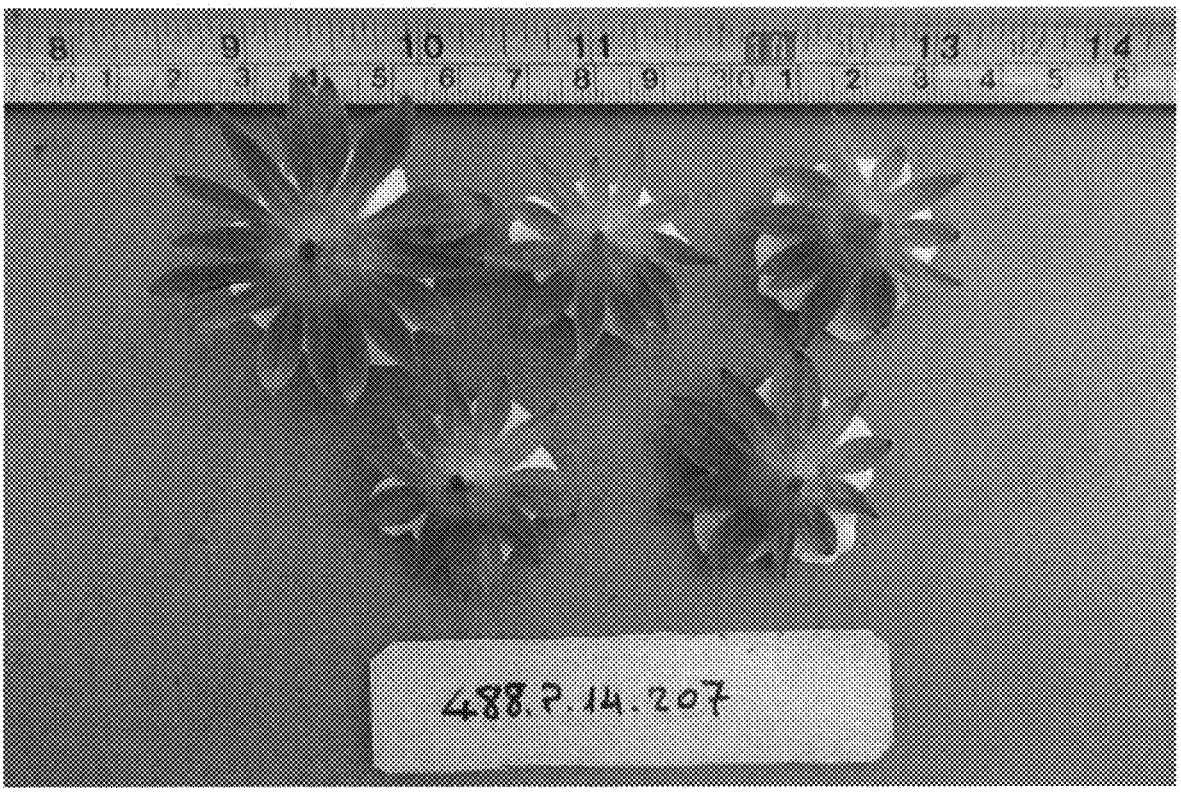

FIG. 8—illustrates specimens of flowers—below, close view (designate in image as 488.P.14.207). Dimensions in centimeters and inches are included.

Figure 9:
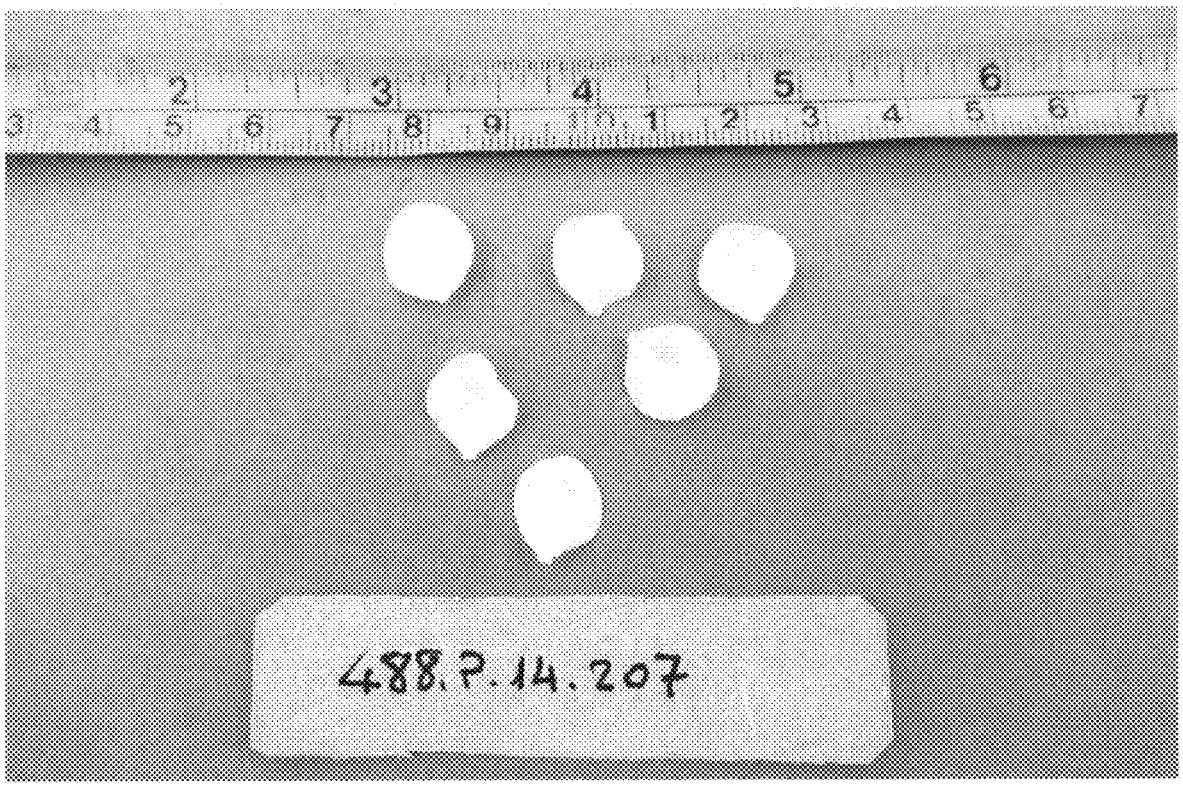

FIG. 9—illustrates specimens of petals of the flowers (designate in image as 488.P.14.207). Dimensions in centimeters and inches are included.

Figure 10:
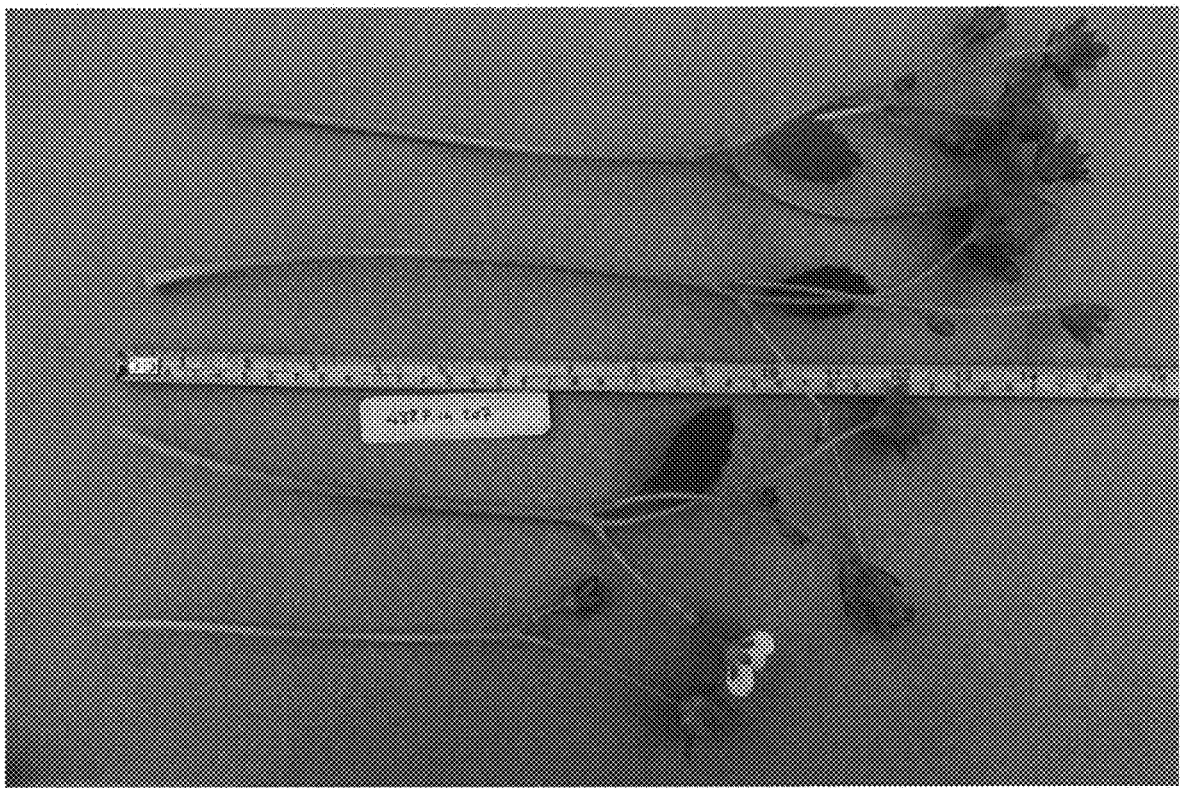

FIG. 10—illustrates specimens of whole inflorescences, including peduncle, pedicel, and leaf (designate in image as 488.P.14.207). Dimensions in centimeters and inches are included.

Figure 11:
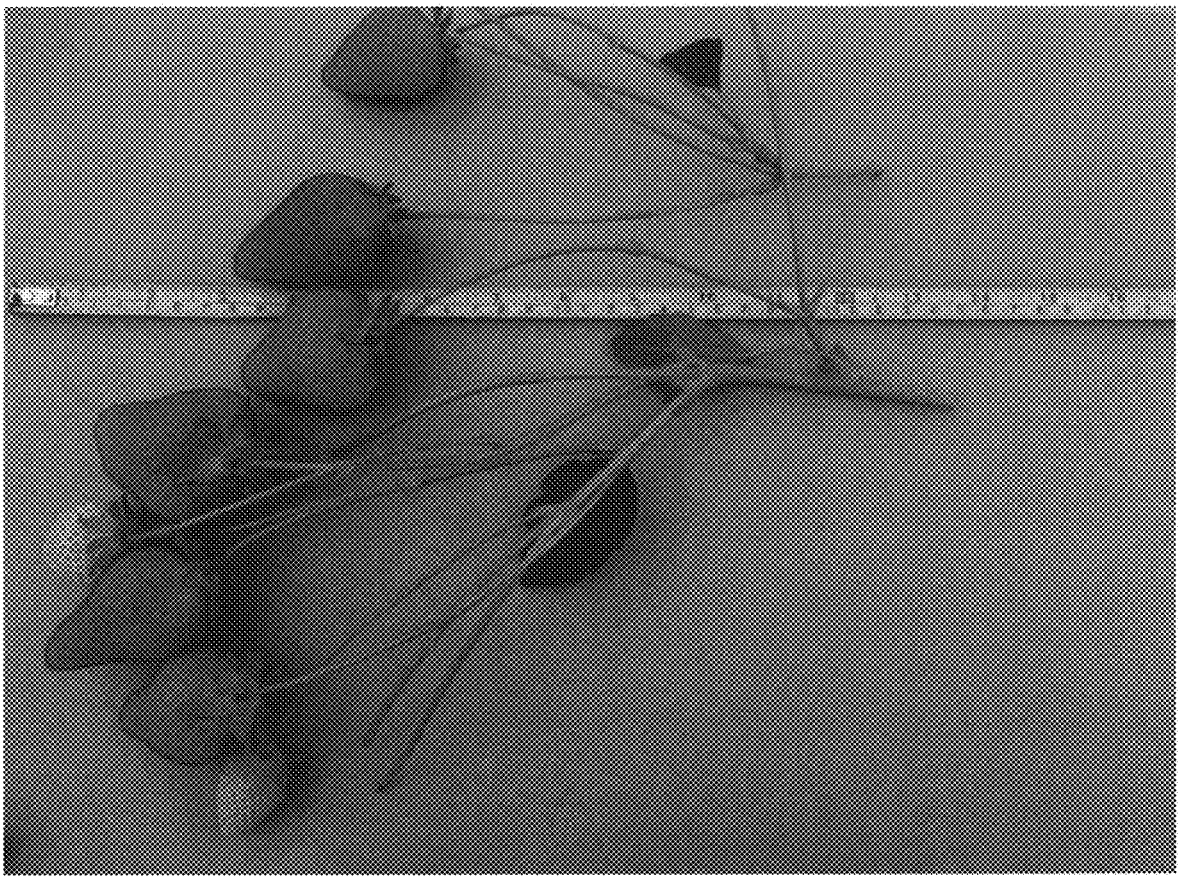

FIG. 11—illustrates specimens of bouquets of fruit, wherein the ensemble of peduncle, pedicels and mature fruits is shown and wherein the difference of sizes between primary and secondary fruits is apparent (designate in image as 488.P.14.207). Dimensions in centimeters and inches are included.

Figure 12:
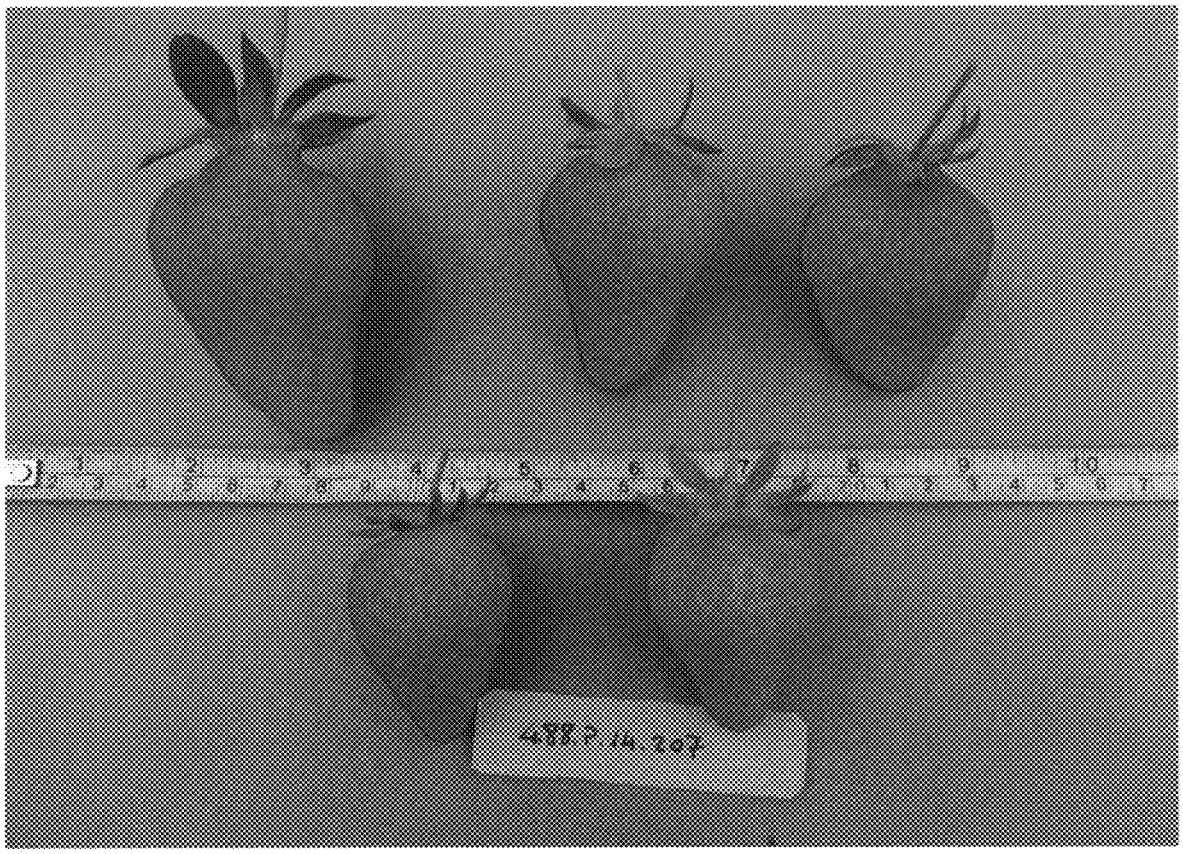

FIG. 12—illustrates specimens of mature fruit—whole (designate in image as 488.P.14.207). Dimensions in centimeters and inches are included.

Figure 13:
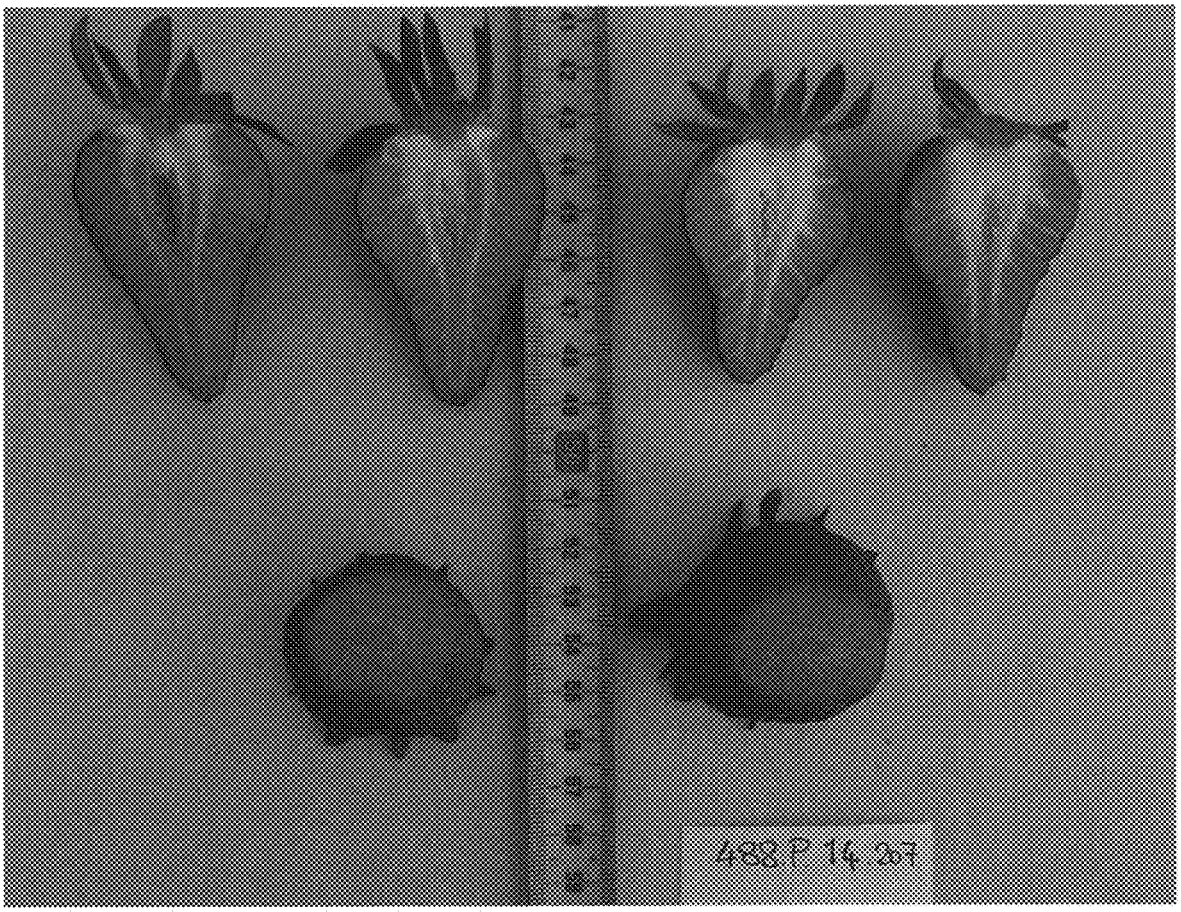

FIG. 13—illustrates specimens of mature fruit—internal sections (designate in image as 488.P.14.207). Dimensions in centimeters and inches are included.

Figure 14:
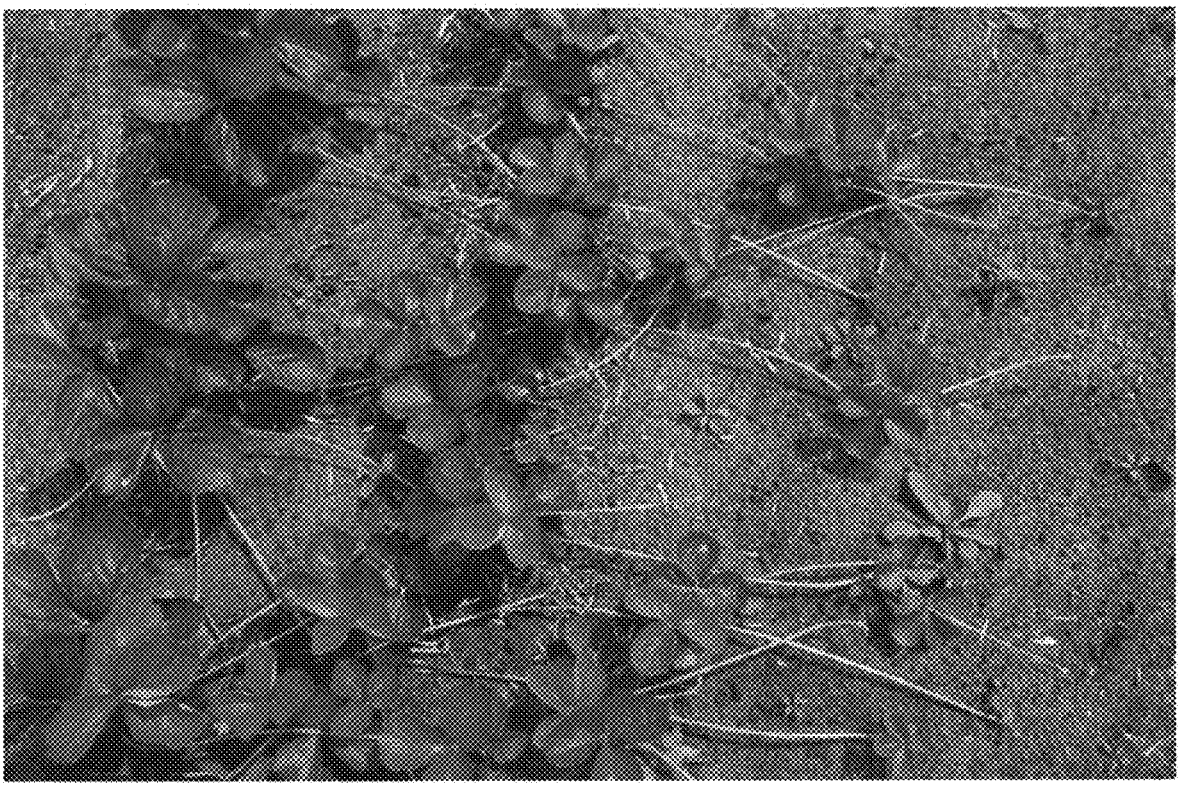

FIG. 14—illustrates specimen of runners (stolons) on Jul. 30, 2018.

DETAILED BOTANICAL DESCRIPTION

The chart used in the identification of colors is that of The Royal Horticultural Society ("R.H.S." Colour Chart), London, England, Edition V. The terminology which precedes reference to the chart has been added to indicate the corresponding color in more common terms. The detailed botanical description is based on plants which were reproduced asexually by the use of stolons at Zielona Gora-Ochla, Poland (located at 51° 848 N-15° 447 E), trasplanted at Nova Siri (MT), Italy (located at 40° 08' 40" N-16° 39' 40" E and 10 meters above sea level) in October and growing under the cover of plastic tunnels.

With regard to stolons, their description took place in Poland. These stolons are derived from frigo plants trasplanted in Poland at Zielona Gora Ochla in April. Therefore the age of the plants on which the botanical description was made is between two and eight months from the transplants.

Plant:

*Type*.—Short-day.

*Configuration*.—Upright and semi-dense.

*Vigor*.—Medium.

*Leaflets number*.—Commonly 3. — size: medium in size, approximately 8.7 cm in length on average, and approximately 8.7 cm in width on average. — terminal leaflet: commonly the same size in length and width, possesses a generally concave cross-section, possesses a serrate to crenate margin, and an acute base. — blistering: commonly is medium to strong in quantity. — glossiness on the upper surface: medium. — color: variegated coloration commonly is absent; upper surface coloration commonly being near Green Group 143A to Green Group N143B; and under surface commonly being near Green Group 138B to Green Group 138C. — texture (upper surface): wrinkled, waxy puncture, presence of tricomas all over the surface. — texture (lower surface): general roughness, trichos mainly present on the ribs. — venation pattern: the main transverse ribs are grafted forming an acute angle, at the insertion level of the main transverse rib there is a curvature in the initial part, there is strong symmetry in the distance between the main transverse ribs.

*Stolons*.—Medium in quantity, sparse pubescence in density, and anthocyanin color is commonly near Red-Purple Group 59B to Red-Purple Group 59C.

*Petioles*.—Elliptical shape, approximately 15 cm to 18 cm in length on average, the average minor axis and the average major axis measured at approximately 3 cm from the base of the stipule is approximately 2.8 mm and 3.3 mm, respectively, color is commonly near Yellow-Green Group 144C to Yellow-Green Group 144B, and commonly bear generally horizontally disposed fine pubescence.

*Stipules*.—Approximately 2.5 cm to 3.2 cm in length on average, the average width of a closed stipules is approximately 10.2 mm, the average width of an open stipules is approximately 21.7 mm, and the color is Yellow-Green Group 145 B, which commonly bears weak to medium anthocyanin coloration of near Red-Purple Group 62A to Red-Purple Group 62B.

*Floral fragrance*.—Medium present.

Inflorescence:

*Flowering time*.—Early, second/third week of December in Nova Siri (MT), Italy (10 meters above sea level).

*Flower disposition*.—Generally above the foliage.

*Flower number*.—Medium, commonly 4 to 8.

*Pedicel hairs*.—Pubescence generally disposed somewhat upwards.

*Pedicel length*.—The average length of the main and secondary pedicles measured from the base of the calyx, with the first fruit already ripe on the main axis is approximately 15 cm.

*Pedicel diameter.—The diameter measured at approximately* 3 cm from the calyx is approximately 2.4 mm.

*Pedicel color*.—Commonly near Yellow-Green Group 144C to Yellow-Green Group 144B.

*Size*.—Large, with primary flowers approximately 3.8 cm to 4.5 cm in diameter on average, and secondary flowers approximately 3.0 cm to 3.8 cm in diameter on average, commonly the open calyx is larger than the diameter; and the length of the inflorescence is approximately 30 cm to 40 cm on average.

*Petals number*.—Approximately 5 to 6 on average, typically 6. — arrangement and shape: generally touching to overlapping, the relationship of the length to the width being slightly longer, and rounded apex. — size: approximately 12 mm on average in length and approximately 10 mm in width on average. — color: commonly near White Group NN155C to White Group NN155D on the upper surface. — texture (upper surface): spongy texture, smooth, glabrous surface, with small translucent points and presence of dimples. — texture (lower surface): slight general roughness which is accentuated at the level of the insertion on the calyx, glabrous and slightly pointed surface.

*Stamens*.—Average number is approximately 25, average length is approximately from 3 mm to 5 mm, color of the filament is Yellow-Green Group 1C.

*Anthers*.—Number is approximately 23 to 28 on average, commonly disposed above the stamen, and color is Yellow Group 11 A.

*Pollen*.—In abundance.

*Stigma*.—Jagged butterfly-shaped, average aperture of approximately 320 μm, dry and waxed, not feathery.

*Style*.—Average length approximately between 1600 μm and 1700 μm, mean diameter of approximately 210 μm, which thins at the level of insertion on the ovary, entirely crossed by a stylus channel with an average diameter of approximately 40 μm, Gynobasic style.

*Ovary*.—Superior, with oval shape and average major axis and the average minor axis of approximately 600 μm and 400 μm.

*Sepals*.—Shape: generally lanceolate in configuration and somewhat outwardly disposed. — number: approximately 9 to 14 on average. — size: approximately 15 mm to 20 mm in length on average, and approximately 5 mm to 8 mm in width on average at the broadest point in primary flowers; and approximately 12 mm to 15 mm in length on average and approximately 4 mm to 6 mm in width at the broadest point on average in secondary flowers. — color: the upper surface is commonly near Green Group 141C to Green Group 141D and the under surface is commonly near Green Group 143A to Green Group 143B. — texture (upper surface): smooth, with waxy marks and trichomes at the edge. — texture (lower surface): slightly wrinkled, presence of tricomes mainly on the basal part.

Fruit:

*Bearing*.—Non-remontant.

*Timing*.—Early fruiting commonly with approximately 28 to 32 days from first blooming to first fruit ripening.

*Shape*.—Conical to slightly rhomboid, slightly longer than broad, commonly with a medium difference between terminal and the other fruits.

*Size*.—Large, with the primary fruit approximately 5.5 cm to 7.5 cm in length on average; approximately 3.5 cm to 3.9 cm in width on average at the broadest point; and approximately 25.7 grams on average.

*Surface*.—Slightly uneven texture with strong glossiness.

*External color*.—Substantially uniform commonly near Orange-Red Group 33A to Orange-Red Group 34A.

*Internal color*.—Flesh is commonly near Orange-Red Group 30B to Orange-Red Group 30A, and the core is commonly near Orange-Red Group 32B to Orange-Red Group 32C.

*Firmness*.—Good firmness.

*Cavity*.—Very small to absent fruit cavity, as illustrated in FIG. 13.

*Achenes*.—Located generally below the fruit surface and cover nearly the entire fruit surface commonly with only a very narrow band (if any) where achenes are absent, and commonly near Orange-Red Group 30B to Orange-Red Group 34A in coloration, depending of fruit maturity.

*Calyx*.—Commonly slightly raised at the point of attachment, the calyx commonly attaches to the fruit with medium adherence, the sepals are disposed generally outwards, calyx typically extends beyond the overlapping petals when open, the fruit diameter and the calyx diameter are commonly equal, and the diameter of the open calyx is commonly greater to that of the corolla.

*Peduncle*.—Very long, approximately 25 cm to 35 cm in length on average including pedicel and flowers, the average minor axis and the average major axis measured at approximately 3 cm from the base in cross section are approximately 3.6 mm and 4.2 mm, respectively, and color is commonly near Yellow-Green Group 144B to Yellow-Green Group 144C.

*Pedicel*.—Commonly with pubescence extending upwards, and color is commonly near Yellow-Green Group 144C to Yellow-Green Group 144B.

*Storability*.—Medium-high.

Development:

*Fertilization*.—Self-fertile.

*Resistance to disease*.—During the time of observations and to date, no sensitivities to any disease were observed.

*Winter hardiness/color tolerance*.—Unknown.

*Drought/heat tolerance*.—Good.

Plants of the 'NSG 207' variety have not been observed under all possible environmental conditions to date. Accordingly, it is possible that the phenotypic expression may vary somewhat with changes in light intensity and duration, cultural practices, and other environmental conditions.

SUPPLEMENTAL COMPARATIVE DATA

Hereafter, additional comparative fruit data is provided for the new variety, the 'Sabrosa' variety, the '488.P.11.10' variety (i.e., the male parent) and the 'SIRIS' variety (i.e., the female variety). The plants were asexually reproduced by the use of stolons in 2017 at Zielona Gora-Ochla, Poland located at 51° 848 N-15° 447 E, and planted in field on Oct. 15, 2017. All varieties were grown under the cover of plastic tunnels at Nova Siri (MT), Italy located at 40° 08' 40" N-16° 39' 40" E (10 meters above sea level). The fruit was first picked on January 23 and last picked on May 30. The fruit were evaluated and compared on the dates indicated. Average data is as follow:

TABLE 1

Accumulated Production of First Quality Fruit (g/plant)

| variety | February 30th | March 30th | April 30th | May 30th |
|---|---|---|---|---|
| 'NSG 207' | 26 | 243 | 501 | 615 |
| 'Sabrosa' | 25 | 129 | 270 | 510 |

TABLE 2

Overall Comparison of Average Fruit Weight

| variety | g/fruit |
|---|---|
| 'NSG 207' | 25.70 |
| 'Siris' | 21.50 |
| '488.P.11.10' | 24.00 |
| 'Sabrosa' | 22.70 |

TABLE 3

Average Fruit Weight on Specified Dates

| variety | March 30th (grams) | April 30th (grams) | May 30th (grams) |
|---|---|---|---|
| 'NSG 207' | 27.4 | 25.1 | 22.3 |
| 'Siris' | 23.7 | 20.5 | 20.0 |
| '488.P.11.10' | 26.1 | 24.5 | 23.0 |
| 'Sabrosa' | 24.4 | 21.0 | 20.4 |

TABLE 4

Fruit Analysis on May 30, 2018

| | 'NSG 207' | 'Sabrosa' | '488.P.11.10' | 'SIRIS' |
|---|---|---|---|---|
| Firmness (average)* | 0.79 | 0.74 | 0.60 | 0.80 |
| Dry Matter (%)** | 8.63 | 8.95 | 7.80 | 8.50 |
| pH (to 202) | 3.51 | 3.81 | 3.55 | 3.75 |
| Acidity as Anhydride Citric (%) | 0.71 | 0.88 | 0.75 | 0.80 |
| Soluble Solids (% Brix) | 7.8 | 9.48 | 8.27 | 9.85 |
| Maturity Index*** | 11.00 | 10.77 | 11.02 | 12.31 |

*Resistance to penetration measured in kilograms using a Turoni (Italy) pentrometer (20 Kg × 0.01).
**Weight of residue from the titration of the fruit after drying at 103° C. until a constant weight is achieved.
***Relation between soluble solids and acidity anhydride.

I claim:

1. A new and distinct strawberry plant characterized by the following combination of characteristics:

(a) exhibits a medium vigor, medium density, and an upright growth habit, (b) displays, on an early basis, white inflorescence at a level generally above the foliage, (c) commonly displays a calyx that is slightly larger than the diameter of the corolla when open, and (d) forms in abundance attractive semi-early-ripening large, medium red primarily conical to slightly rhomboid fruit having firm flesh that is longer than broad in configuration;

substantially as herein shown and described.

* * * * *